| United States Patent [19] | [11] | 4,170,711 |
|---|---|---|
| Orlando et al. | [45] | Oct. 9, 1979 |

[54] BROMINATED BIPHENOL DERIVATIVES

[75] Inventors: Charles M. Orlando, Schenectady, N.Y.; Francois A. Lavallee, Willoughby Hills, Ohio

[73] Assignee: General Electric Company, Schenectady, N.Y.

[21] Appl. No.: 726,617

[22] Filed: Sep. 27, 1976

Related U.S. Application Data

[63] Continuation of Ser. No. 450,334, Mar. 12, 1974, abandoned, which is a continuation-in-part of Ser. No. 169,517, Aug. 5, 1971, Pat. No. 3,929,908.

[51] Int. Cl.$^2$ ............................................. C07C 43/22
[52] U.S. Cl. ..................... 568/610; 568/643; 568/730; 106/15 FP; 252/8.1; 260/45.95 R; 260/77.5 D; 260/348.49; 260/465 G; 260/DIG. 24; 560/141; 560/85; 260/586 R; 260/590 R; 260/463; 260/453 AR; 260/609 R; 260/503; 260/505 R; 260/513 R; 260/553 R
[58] Field of Search ....................... 260/613 B, 613 R

[56] References Cited

U.S. PATENT DOCUMENTS

| 3,306,875 | 2/1967 | Hay ............................... 260/613 R X |
| 3,330,781 | 7/1967 | Gemeinhardt ................ 260/613 B X |
| 3,544,637 | 12/1970 | Kober et al. ...................... 260/613 B |
| 3,929,908 | 12/1975 | Orlando et al. ....................... 260/620 |

FOREIGN PATENT DOCUMENTS 1030624  5/1966  United Kingdom ................. 260/613 B Primary Examiner—Bernard Helfin
Attorney, Agent, or Firm—F. Wesley Turner; Joseph H. Cohen; Charles T. Watts

[57] ABSTRACT

Monomeric and polymeric halogenated organic compounds derived from 2,2',6,6'-tetrabromo-3,3',5,5'-tetraalkyl-4,4'-biphenols are described. The derivatives are useful in their monomeric and polymeric form as flame retardant additives and/or concentrates for normally flammable resinous materials. The thermal stability at elevated temperatures of the brominated biphenol derivatives advantageously benefits polymeric compositions containing the brominated biphenol derivatives especially when the polymeric compositions are molded into three dimensional articles, or formed into films, sheeting or shaped into fibers, laminates or reinforced plastics by conventional techniques.

7 Claims, No Drawings

BROMINATED BIPHENOL DERIVATIVES

This is a continuation, of application Ser. No. 450,334, filed Mar. 12, 1974 and now abandoned which in turn is a continuation-in-part of application Ser. No. 169,517, filed Aug. 5, 1971 and now U.S. Pat. No. 3,929,908.

This invention relates to monomeric and polymeric halogenated organic compounds of the formula: (I.)

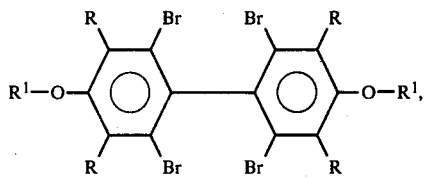

wherein each R independently is selected from primary alkyl groups, each $R^1$ is independently selected from hydrogen and organic groups, at least one $R^1$ being an organic group.

In our copending application, Ser. No. 169,517, filed Aug. 5, 1971, and assigned to the same assignee as the present invention, we disclosed the preparation of 2,2',6,6'-tetrabromo-3,3', 5,5'-tetraalkyl-4,4'-biphenol (hereinafter sometimes referred to as TATB) by reacting a 3,3',-5,5'-tetraalkyl substituted diphenoquinone with bromine and the subsequent conversion of the monomeric derivatives into reactive monomeric materials suited to the preparation of polyesters, polycarbonates, epoxy resins, polyethers, etc. These materials are useful as fire-retardant additives for polymeric compositions, and are useful in the preparation of flame-retardant polymeric compositions having bromine constituents integrated within the skeletal backbone of the polymer structure.

Although other halogenated biphenols, including monomeric and polymeric derivatives thereof, such as bisphenol-A and those derived from bisphenol-A are well-known to the art, the tetraalkyltetrabromobiphenol derivatives of our invention are advantageously employed in the preparation of fire-retardant polymeric compositions because of the unexpected thermal stability associated with the molecular arrangement found within the 2,2',6,6'-tetraprimaryalkyl-3,3'-5,5'-tetrabromo-4,4'-biphenyldioxy molecular structure. Quite unexpectedly, it has been found that the polymeric entity associated with the halogenated biphenols derivatives described herein are more thermally stable at elevated temperatures than other well-known halogenated biphenols, such as bisphenol-A, and derivatives thereof.

Although we do not wish to be bound by our theory, we believe that the symmetrical oxygen-alkyl-bromine-biphenyl spatial relationship associated with the TATB of formula (I.) is such a spatial relationship that compositions containing such a molecular arrangement are especially stable against thermal degradation at elevated temperatures. This resistance to thermal degradation, as evidenced by the lack of discoloration of polymeric compositions containing such molecular configurations, is noticeable when the discoloration of similar polymeric compositions containing other halogenated biphenols are mixed especially at temperatures comparative within the range of from about 200° C. to as high as 550° C., or even higher.

For illustrative purposes, the difference in thermal stability of 2,2',6,6'-tetramethyl-3,3',5,5'-tetrabromo-4,4'-biphenol (hereinafter sometimes referred to as TTB) and 2,2'-bis(3,5-dibromo-4-hydroxyphenyl) propane (hereinafter sometimes referred to as tetrabrominated bisphenol-A (TBBPA) are illustrated by the percentage weight losses associated with the aforementioned halogenated biphenols when each is separately heated at 10° C. per minute under TGA test conditions in (a) the presence of air and (b) in the presence of nitrogen set out hereafter.

| (1) TGA DATA-TTB | | | | | | | |
|---|---|---|---|---|---|---|---|
| (a) AIR (10° C./ min.) | | | | | | | |
| Weight Loss | 1% | 5% | 10% | 25% | 50% | 75% | 95% |
| Temp. °C. | 260 | 295 | 312 | 370 | 448 | 493 | 527 |
| (b) N₂(10°/ min.) | | | | | | | |
| Weight Loss | 1% | 5% | 10% | 25% | 50% | 75% | 95% |
| Temp. °C. | 240 | 270 | 280 | 298 | 312 | 325 | 510 |
| (2) TGA DATA-TBBPA | | | | | | | |
| (a) AIR (10° C./min.) | | | | | | | |
| Weight Loss | 1% | 5% | 10% | 25% | 50% | 75% | 95% |
| Temp. °C. | 245 | 275 | 280 | 310 | 315 | 340 | 510 |
| (b) N₂(10° C./min.) | | | | | | | |
| Weight Loss | 1% | 5% | 10% | 25% | 50% | 75% | 95% |
| Temp. °C. | 245 | 275 | 280 | 320 | 330 | 370 | 770 |

From the above TGA thermal decomposition data, TTB is more stable than TBBPA at temperatures within the range of from about 240° to about 530°, temperatures well within the range at which many resins and plastic materials are substantially thermally decomposed to monomeric materials, e.g. polyacrylonitrile, (250° C.); polymethylmethacrylate (350° C.); polystyrene (350° C.); polyalphamethylstyrene (350° C.); polyisoprene (370° C.); poly-n-methylstyrene (390° C.); polyisobutylene (400° C.); polyvinylacetate (280° C. under vacuum), polyacrylonitrile (350° C. in the presence of nitrogen; polypropylene (410° C. under vacuum); polyvinylchloride (440° C. in the presence of nitrogen); polyvinylidene chloride (440° C. in the presence of nitrogen); polybutadiene (420° C. under vacuum), and polyethylene (475° C. under vacuum), etc.

In accordance with this invention, we have found that novel monomeric and polymeric halogenated organic compounds of the formula:

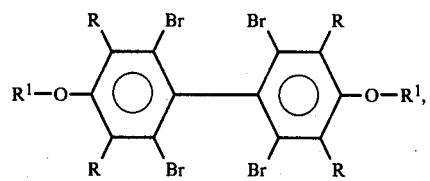

wherein each R independently is selected from primary alkyl groups, each $R^1$ is independently selected from hydrogen and organic groups, and at least one $R^1$ is an organic group.

Representative of monomeric halogenated organic compounds included within the scope of the above formula are 2,2',6,6'-tetrabromo-3,3',5,5'-tetraalkyl-4,4'-biphenol derivatives wherein each $R^1$ independently is selected from the radicals consisting of:

(i) organic radicals, such as (a) R²—

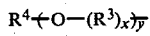

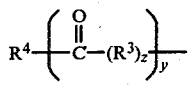

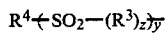

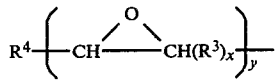

wherein R² is selected from the group consisting of hydrogen, cyano, alkyl, alkenyl, cycloalkyl, cycloalkenyl, aryl and mixtures thereof, such as alkylaryl, alkylcycloalkyl, arylalkyl, alkenylaryl, alkenylcycloalkyl, arylcycloalkyl, arylalkenyl, etc., R³ is selected from the group consisting of alkylene, cycloalkylene, arylene and mixtures thereof, such as alkylcycloalkylene, alkylarylene, etc., R⁴ is selected from the group consisting of hydrogen, alkyl, alkenyl, cycloalkyl, cycloalkenyl, aryl and mixtures thereof, such as alkylaryl, alkylcycloalkyl, arylalkyl, alkenylaryl, alkenylcycloalkyl, arylcycloalkenyl, arylalkenyl, etc., x is a positive integer of at least 1, y is a positive integer of at least 1, and z is a positive integer of at least 0. Preferably, the organic hydrocarbyl radicals represented by R², R³ and R⁴ contain from about 1 to about 10 carbon atoms, and more preferably contain from about 1 to about 5 carbon atoms. Among the derivatives included within the above organic groups are such compounds as 4,4'-bis(2-hydroxyethoxy)-2,2',6,6'-tetrabromo-3,3',5,5'-tetramethylbiphenyl (for purposes of brevity sometimes hereafter the phrase 2,2',6,6'-tetrabromo-3,3',5,5'-tetramethylbiphenyl will be referred to as TTBP); 4-hydroxy-4'(2-hydroxyethoxy)-TTBP; 4-(2-hydroxyethoxy)-4'[2-(2-hydroxyethoxy)-ethoxy]-TTBP; 4,4'-diacetoxy-TTBP phenyl; 4,4'-dihydroxy-TTBP-diglycidylether; 4,4',diallyloxy-TTBP; 4,4'dicyanato-TTBP; 4,4'-diaryloyloxy-TTBP; 4,4'-bis(2-hydroxypropoxy-TTBP; 4,4'-bis(4-hydroxycyclohexoxy)-TTBP; 4,4'-bis(4-hydroxy-phenoxy)-TTBP; 4,4'-bis(4-hydroxydecyloxy)-TTBP;4,4'-bis(7-hydroxynaphthoxy)-TTBP; 4-hydroxy-4'-(2-hydroxyethoxy)-TTBP; 4-hydroxy-4'-(4-cyclohexyloxy)-TTBP, 4-hydroxy-4'-(hydroxyphenoxy)-TTBP, 4-hydroxy-4'-(4-hydroxydecyloxy)-TTBP, 4-hydroxy-4'-(hydroxynaphthoxy)-TTBP, etc.

As disclosed in our copending application Ser. No. 169,517, filed Aug. 5, 1971, referred to hereinbefore TTB derivatives such as 4,4'-bis(2-hydroxyethoxy)-2,2',6,6'-tetrabromo-3,3',5,5'-tetramethylbiphenyl can be converted readily to esters of monocarboxylic acids, can be reacted with ethylene oxide to form 4,4'-bis(2-hydroxyethoxy)-2,2',6,6'-tetrabromo-3,3',-5,5'-tetramethylbiphenyl which in turn can be incorporated into either polyesters or polycarbonates or made into plasticizers, can be reacted with epichlorohydrin to form 4,4'-dihydroxy-2,2',-6,6'-tetrabromo-3,3',5,5'-tetramethylbipheny diglycidylether which is useful in making epoxy resins, can be reacted with a mixture of acetic acid and acetic anhydride to prepare the diacetate ester, i.e., 4,4'-diacetoxy-2,2',6,6'-tetrabromo-3,3',5,5'-tetramethylbiphenyl, can be reacted with allyl chloride to prepare 4,4'-diallyloxy-2,2',6,6'-tetrabromo-3,3',5,5'-tetramethyl -tetramethylbiphenyl, can be reacted with cyanogen bromide to replace both hydroxy groups with a -CN groups in the preparation of 4,4'-dicyanato-2,2',6,6'-tetrabromo-3,3',5,5'-tetramethylbiphenyl, etc.

As previously pointed out in our copending application, Ser. No. 169,517, referred to hereinbefore, the monomeric reactant 4,4'-diallyloxy-TTBP and a 4,4'-dicyanato-TTBP can be polymerized when heated with or without a polymerization catalyst, either alone or with other polymerizable monomers into useful polymers. 4,4'-diacetoxy-TTBP can readily be converted to epoxy resins, either alone or with other epoxides, by reaction with monomeric or polymeric diols in the presence of polyamine or anhydride catalysts. The 4,4'-bis(2-hydroxyethoxy)-TTBP can be reacted to form polyesters with dicarboxylic acid esters by ester interchange with low molecular weight glycols, e.g., 1,4-butanediol, etc., polyesters of terephthalic acid in the presence of a transesterification catalyst to produce homopolymers as well as copolyesters. These polyesters like other polymers described hereinbefore have fire-resistant properties, per se, or can be blended with other polymers to impart flame resistant properties to the blend. The disclosure of the flame-retardant additive property as well as flame retardant resistant properties of such polymers or polymer blends is more fully described in our copending application Ser. No. 450,364, filed Mar. 12, 1974, filed concurrently herewith, assigned to the same assignee as the present invention, which is hereby incorporated herein by reference in its entirety.

The following examples illustrate the preparation of the 2,2',6,6'-tetrabromo-3,3',5,5'-tetraalkyl-4,4'-biphenol derivatives which are within the scope of this invention. They are not to be construed, however, to limit the scope of our invention in any manner whatsoever.

EXAMPLE I

Preparation of 4,4'-bis82-hydroxyethoxy)-2,2',

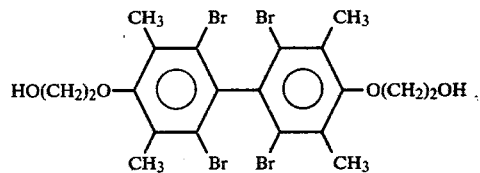

A solution of 2,2',6,6'-tetrabromo-3,3',5,5'-tetramethylbiphenol (400 g., 0.718 mole) and sodium hydroxide (65.2 g., 1.63 mole, 2.27 molar equivalents) in 600 ml. of deaerated 50% acqueous ethanol was heated at reflux under nitrogen for 30 minutes. Deaerated distilled ethylene chlorohydrin (237 g., 2.94 mole) was added slowly to this hot solution and the resulting mixture was heated for one hour. About 30 minutes into this reflux period, an additional 200 ml. of deaerated 95% ethanol was added to partially redissolve a solid which had formed (some sodium chloride remains precipitated). After the one hour reflux period, an additional 65.2 g. (1.63 mole) of sodium hydroxide and 50 ml. of deaerated water were added and the mixture refluxed for 30 minutes. Ethylene chlorohydrin (237 g., 2.94 mole) was added slowly and this mixture heated for 75 minutes. Sodium hydroxide (100 g., 2.5 mole), deaerated water (200 ml.) and deaerated 95% ethanol (450 ml.) were added, and this mixture refluxed for 45 minutes. A final portion of ethylene chlorohydrin (474 g., 5.88 mole) was added and this mixture refluxed for 75 minutes.

Deaerated water (3 liters) was then added to the vigorously stirred mixture and, while still stirring, the mixture was allowed to cool. After standing overnight, the crystals were filtered and dried in vacuo for 4 hrs./100°C. The product was recrystallized from 500 ml. of methanol giving, after vacuum drying, 322.0 g. of the diol 4,4′-bis(2-hydroxyethoxy)-TTBP, m.p. 170°–172° C. Additional product was obtained from the original reaction mixture totaling 137.7 g. The total yield of product was 99.3%.

EXAMPLE II

Preparation of 4,4′-bis(2-hydroxyethoxy)-2,2′,6,6′-tetrabromo-3,3′,5,5′-tetramethylbiphenyl

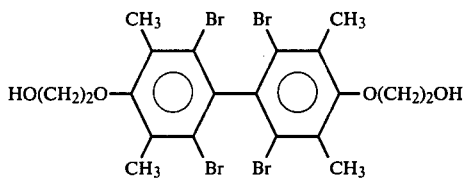

2,2′,6,6′-tetrabromo-3,3′,5,5′-tetramethylbiphenol (2.00 g., 3.59 mole) and triethylamine (34 mg., 0.34 mole) in 3 ml. of diethyl carbitol ($CH_3CH_2OCH_2CH_2$-)$_2$O) were heated to 175°. Ethylene oxide was then bubbled through the solution. Solvent was added as necessary to maintain the volume and an additional 34 mg. of triethylamine was added after the first 34 hours. The progress of the reaction was monitored by TLC, and at the end of the 53 hours, the reaction product consisted essentially of 4,4′-bis(2-hydroxyethoxy)-TTBP with only traces of the monohydroxyethylated material 4-hydroxy-4′-(2-hydroxyethoxy)-TTBP and the product of further reaction, 4-(2-hydroxyethoxy)-4′[2-(hydroxyethoxy)ethoxy]-TTBP.

EXAMPLE III

Preparation of 4-hydroxy-4′-(2-hydroxyethoxy)-2,2′,6,6′-tetrabromo-3,3′,5,5′-tetramethylbiphenyl

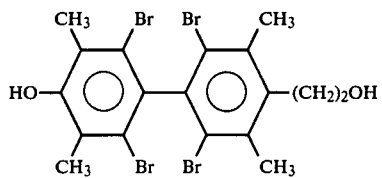

A mixture of 2,2′,6,6′-tetrabromo-3,3′,5,5′-tetramethylbiphenol (9.9 g., 0.0177 mole), sodium hydroxide (0.8 g., 0.02 mole), 10 ml. water and 10 ml. 95% ethanol was refluxed for 30 minutes. Ethylene chlorohydrin (10 ml., 11.8 g., 0.147 mole) was added and the mixture refluxed for 90 minutes. Crystals formed from the hot solution were filtered to give 7.8 g. of a product. This solid was recrystallized several times from benzene affording, after drying, 3.5 of 4-hydroxy-4′-(2-hydroxyethoxy)-TTBP, m.p. 235°–41°. TLC analysis of this purified product indicated a small amount of 4,4′-bis(2-hydroxyethoxy)-TTBP as an impurity. A second crop of crystals, 1.6 g. m.p. 234°–239°, provided a total yield of product of 51%.

EXAMPLE IV

Preparation of 4-(2-hydroxyethoxy-4′[2-(2-hydroxyethoxy)ethoxy]-2,2′,6,6′-tetrabromo-3,3′,5,5′-tetramethylbiphenyl

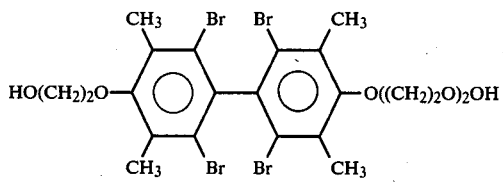

In a procedure similar to that described above for the preparation of 4,4′-bis(2-hydroxyethoxy)-TTBP in Example I, 200 g. of 2,2′,6,6′-tetrabromo-3,3′,5,5′-tetramethylbiphenol was treated a total of four times with sodium hydroxide and ethylene chlorohydrin. The resultant material (227 g.) was recrystallized from benzene (400 ml.), affording a mother liquor rich in 4-(2-hydroxyethoxy)-4′-[2-(2-hydroxyethoxy)ethoxy]-TTBP and crystals rich in 4,4′-bis(2-hydroxyethoxy)-TTBP. The crystals were recrystallized from benzene (350 ml.) to afford 157 g. (68%) of 4,4′-bis(2-hydroxyethoxy)-TTBP m.p. 169.5°–171.5° C. The mother liquor rich in 4,(2-hydroxyethoxy)-4′- 2-(2-hydroxyethoxy)-TTBP was evaporated to a solid which after recrystallization (3 times) from methanol (40 ml., −28° C.) gave 34 g. of solid. This product was predominantly 4-(2-hydroxyethoxy)-4′- 2-(2-hydroxyethoxy)-TTBP. Several further recrystallizations from methanol (−28° C.) afforded 4.3 g. of 4-(2-hydroxyethoxy)-4′-[2-(2-hydroxyethoxy)ethoxy]-TTBP m.p. 121°–126° C.

EXAMPLE V

Preparation of 4,4′-diacetoxy-2,2′,6,6′-tetrabromo-3,3′,5,5′-tetramethylbiphenyl.

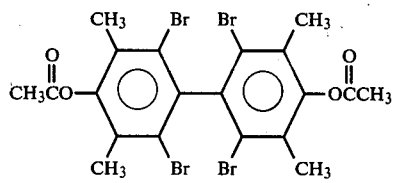

A solution of 2.0 g. (0.00358 mole) of 2,2′,6,6′-tetrabromo-3,3′,5,5′-tetramethylbiphenol (TTB) in 1 ml. of acetic anhydride and 25 ml. of acetic acid was refluxed for 2 hours. The mixture was poured into 100 ml. of water and extracted with carbon tetrachloride. The extract was dried (MgSO$_4$), filtered and evaporated to a solid which was recrystallized from methanol to give the diacetate 4,4′-diacetoxy-TTBP, 1.7 g. (75%), m.p. 183°–185° C.

EXAMPLE VI

Preparation of 4,4'-dihydroxy-2,2',6,6'-tetrabromo-3,3',5,5'-tetramethylbiphenyl diglycidylether.

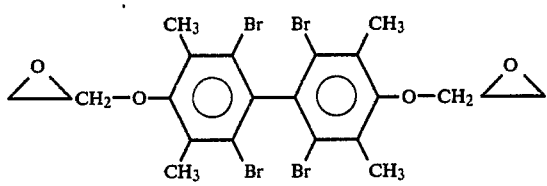

A solution of 0.83 g. (0.036 mole) of sodium in 30 ml. of methanol was prepared and 7.9 g. (0.014 mole) of TTB was added. The resulting solution was heated and the methanol was distilled off and gradually replaced by 20 ml. of benzene. The reaction mixture was finally brought to dryness by distilling off all of the benzene. A total of 11.8 g. (0.127 mole) of epichlorohydrin was added to the solid and the resulting mixture was refluxed for 1 hour. The reaction mixture was cooled and diluted with a 1:1 mixture of $CCl_4$ and water. The $CCl_4$ layer was separated, dried ($MgSO_4$) and evaporated to dryness. The residue was diluted with methanol, filtered free of some insoluble solid and heated to boiling. Water was added to the hot methanol solution until turbid and cooled to give crystals of 4,4'-dihydroxy-TTBP-diglycidyether, 4.6 g. (50%), m.p. 146°–147°C.

EXAMPLE VII

Preparation of 4,4'-diallyloxy-2,2',6,6'-tetrabromo-3,3',5,5'-tetramethylbiphenyl.

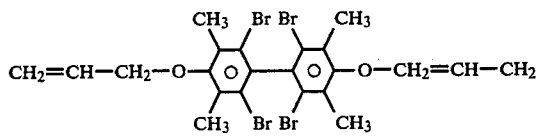

A mixture of 11.59 g. (0.02 mole) of TTB, 4.0 g. (0.052 mole) of allyl chloride and 7.0 g. (0.052 mole) of potassium carbonate in 50 ml. of dry acetone was refluxed for 10 hours. The reaction mixture was diluted with 100 ml. of water and extracted with three 50 ml. portions of ether. The ether extracts were combined and dried ($MgSO_4$), filtered and evaporated to a solid. This solid was recrystallized from methanol to give needles of 4,4'-diallyloxy-TTBP, 5.0 g. (40%), m.p. 120°–123° C.

EXAMPLE VIII

Preparation of 4,4'-dicyanato-2,2',6,6'-tetrabromo-3,3',5,5'-tetramethylbiphenyl.

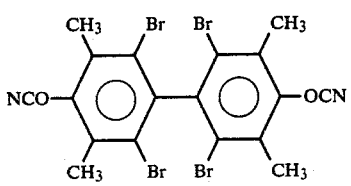

A mixture of 1 g. (0.0017 mole) of TTB and 0.4 g. (0.0037 mole) of cyanogen bromide in 50 ml. of acetone was cooled in an ice-water bath and stirred at this temperature for 30 minutes. A solution of 0.5 g. (0.005 mole) of triethylamine in 4 ml. of acetone was then added to the reaction mixture. Upon addition of the amine solution, a solid precipitated. The entire mixture was stirred at ice-water temperature for an additional 2 hours. The reaction mixture was filtered and the filtrate evaporated to a solid which was recrystallized from 95% ethanol to give crystals of 4,4'-dicyanato-TTBP, 0.67 g. (65%), m.p. 226°–228° C.

EXAMPLE IX

Preparation of 4,4'-bis(acryloyloxy)-2,2',-6,6'-tetrabromo-3,3',5,5'tetramethylbiphenyl.

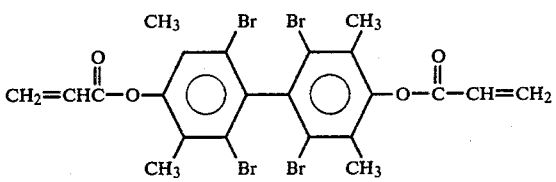

Under nitrogen, 558 g. of TTB (1.00 mole) was suspended in 2 l. of deaerated benzene (ACS grade) in a 5 l. flask equipped with a dropping funnel, a mechanical stirrer and a cooling bath. Deaerated triethyl amine (350 ml., Eastman white label) was added, causing the temperature to jump from 23° to 35°. Freshly distilled deaerated acryloyl chloride (217 g., 2.40 moles) was then added over 30 minutes while cooling so as to maintain a temperature of 45°–50°. The suspension was then stirred at 42° for an additional 30 minutes, cooled to room temperature, and filtered through scintered glass to remove the hydrchloride. The filter cake was washed with benzene, and the wash added to the rest. The analysis showed only a single spot (silica gel, 1 elution $CHCl_3$, bisacrylate $R_f=0.70$, TTB reference $R_f=0.36$; 1 elution $CH_2Cl_2$, bisacrylate $R_f=0.55$). The solvent was removed on a rotary evaporator, affording a crystalline mass. The material was taken up in 3.1 of dichloromethane and filtered through 2 kg. of silica gel slurry packed in dichloromethane. The last of the material was washed off the column with an additional 3 l. of dichloromethane. The solvent was removed on a rotary evaporator and the product recrystallized from 400 ml. of dichloromethane at 3°. The crystals were filtered, washed with a small amount of cold 2:1 dichloromethane/ hexane, and dried in a vacuum oven at 100° to constant weight, affording a first crop of 547 g., 82% yield, of 2,2',6,6'-tetrabromo-3,3',5,5'-tetramethylbiphenyl bisacrylate, also appropriately described as 4,4'-bis-(acryloyloxy)-TTBP, m.p. 200°–201°.

EXAMPLE X

Incorporation of 4,4'-bis(acryloyloxy)-TTBP into a poly(methylmethacrylate)

4,4'-Bis(acryloyloxy)-TTBP (4.0 g.) was dissolved in 28 g. of a 35% solids solution of poly(methylmethacrylate) in methyl methacrylate which is stable indefinitely at 40° F. The material contains a sensitizer which kicks off a radical initiator at room temperature. An initiator is added just before the polymerization reaction is desired. The initiator was added and the material poured into a mold. After 1.5 hours, the material (which still smelled slightly of monomer) was placed in an oven at 60° for an additional 2 hours to afford the final crosslinked polymer. The crosslinked nature of the material was illustrated by its insolubility on stirring at room temperature in chloroform for 5 days to contrast to the behavior of a comparison piece of uncrosslinked material.

The copolymer of 4,4'-bis(acryloyloxy)-TTBP/methylmethacrylate was evaluated to determine its fire-retardant polymeric property, in accordance with the oxygen index test described by ASTM test method D-2863, and exhibited an oxygen index value of 18.3 whereas the homopolymer of methylmethacrylate had an oxygen index of 17.4. Although an increase of oxygen index was relatively small, the increase in the value of the oxygen index to 18.3 versus the 17.4 value for non-brominated polyacrylate polymer substantiates the conclusion that the flammability characteristics of the brominated polyacrylate had been reduced to some measureable degree by the inclusion of the bromine containing TTB derivatives in the polymer skeletal structures.

EXAMPLE XI

Preparation of TTB/bisphenol-A polycarbonates

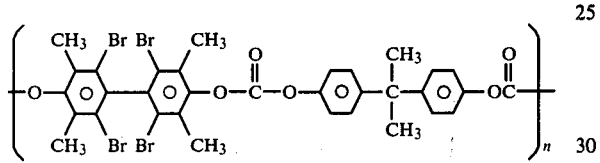

A polycarbonate was prepared from 2,2', 6,6'-tetramethyl-3,3',5,5'-tetrabromo-4,4'-biphenyl by interfacial polymerization with bisphenol-A bischloroformate according to the following procedure: 2.79 gm. of TTB, 100 ml. of 0.2 N aqeuous sodium hydroxide, 0.2 gm. of benzyltriphenylphosphonium chloride, 0.1 g. sodium hydrosulfite and 5 ml. of methylene chloride were vigorously agitated in a blender, and one equivalent of bisphenol-A bischloroformate in 50 ml. of methylene chloride added. The resultant polymer was precipitated in methanol and dried. The material having an I.V. (CHCl$_3$) of 0.84 dl/g., and an n value of was cast into a clear thin film.

The resulting resin, on molding, discolored at 740° F., which is the temperature at which the base resin discolors and decomposes. By way of contrast, tetrabromobisphenol-A/bisphenol-A polycarbonates streaks (discolors) at a temperature between 650° and 700° F. The lack of discoloration at 740° F. of polycarbonates containing the TTBP molecular unit in contrast to the discoloration at temperatures of 650°–750° F. for polycarbonates containing the tetrabromobisphenol-A molecular unit exemplifies the distinct thermal and color stability of the polymeric derivatives of TTB in contrast with the thermal and color stability of other polymeric materials derived from other well-known halogenated biphenol monomer reactants.

EXAMPLE XII

Terephthalate polyesters of butanediol and 4,4'-bis(2-hydroxyethoxy)-2,2',6,6'-tetrabromo-3,3',5,5'-tetramethylbiphenyl.

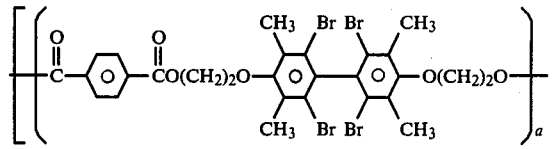

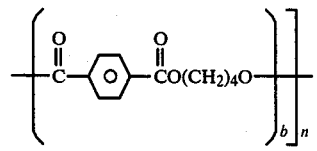

4,4'-bis(2-hydroxyethoxy)-2,2',-6,6-tetrabromo-3,3',5,5'-tetramethylbiphenyl was prepared in accordance with the process described in Example I. A series of polyesters derived from (1) a poly(butyleneterephthalate) prepolymer having an intrinsic viscosity of 0.14 dl/g and (2) 4,4'-bis(2-hydroxyethoxy)-TTBP were copolymerized by melt polymerization in a small screw reactor at temperatures within the range of from 200°–240° C. in the presence of a titanate-ester catalyst. The terephthalate acid esters were prepared with varying diol content in order to vary the bromine content of the resulting polymer as well as to determine its effect upon the polymer's molecular intrinsic viscosity, glass transition temperature in relationship to the TTB diol content and/or the butanediol content of the polyester. Table I set out hereafter shows the composition, reaction conditions and some of the properties of the series of polyester polymers ranging from poly(butyleneterephthalate) homopolymer to the copolymer derived from terephthalate acid and bis(hydroxyethoxy)tetramethyltetrabromobiphenyl.

EXAMPLE XII - TABLE I

Properties of Bis(hydroxyethoxy)Tetrabromotetramethylbiphenyl-Butanediol-Terephthalic Acid Homopolymers and Copolymers

| No. | Mole %[a] Diol II | % Br | Polymerization time (hrs) | Polymerization temp (°C.) | Polymerization pressure (mm Hg) | I.V.[b] | Tg | Tm[c] (° C.) |
|---|---|---|---|---|---|---|---|---|
| 1 | 100 | 41.2 | 5.3 | 265 | 0.20 | 0.13 | 143° | N.O. |
| 2 | 95 | 40.6 | 5.0 | 260 | 0.35 | — | — | — |
| 3 | 80 | 38.5 | 5.0 | 265 | 0.20 | 0.18 | 138° | N.O. |
| 4 | 50 | 32.1 | 5.5 | 270 | 0.20 | 0.29 | 109° | N.O. |
| 5 | 20 | 19.3 | 4.0 | 268 | 0.20 | 0.60 | 70° | N.O. |
| 6 | 8 | 9.6 | 6.2 | 240 | 0.25 | 0.80 | N.O. | 210 |
| 7 | 8 | 9.6 | 4.0 | 260 | 0.20 | 0.86 | — | — |
| 8 | 8 | 9.6 | 1.5 | 280 | 0.15 | 0.72 | — | — |

EXAMPLE XII - TABLE I-continued

Properties of Bis(hydroxyethoxy)Tetrabromotetramethylbiphenyl-Butanediol-Terephthalic Acid Homopolymers and Copolymers

| No. | Mole %[a] Diol II | % Br | Polymerization time (hrs) | Polymerization temp (°C.) | Polymerization pressure (mm Hg) | I.V.[b] | Tg | Tm[c] (°C.) |
|---|---|---|---|---|---|---|---|---|
| 9 | 0 | 0 | 3.0 | 270 | 0.15 | 0.64 | 22° | 225 |

N.O.=Not Observed
[a]=Based on mole % diol II + mole % butanediol = 100% of the diols in the final polymer
[b]=Run in 60/40 phenol/tetrachloroethane
[c]=Determined by DSC An advantage in the employment of the TTB derivatives in the preparation of the terephthalate esters set out hereinbefore is associated with the fact that the polymerization process can be carried out at temperatures of 240°–280° C.

EXAMPLE XIII

Preparation of a cyanurate from the biscyanate ester of tetrabromotetramethylbiphenol.

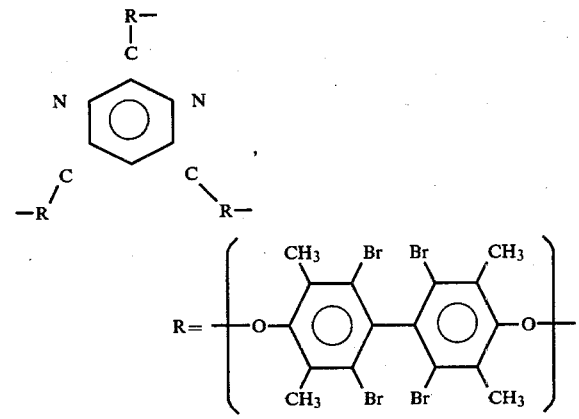

4,4'-dicyanato-2,2',6,6'-tetrabromo-3,3',5,5-tetramethylbiphenyl—prepared in accordance with the procedure set out in Example VIII, hereinbefore, was slowly heated from room temperature to about 300° C. over a period of one hour to form the cyanurate of the formula set out above. The cyanurate polymer when cooled formed a powder which was insoluble in acetone, alcohol or chloroform.

EXAMPLE XIV

Preparation of a polyurethane from 4,4'-bis(2-hydroxyethoxy)-2,2',6,6'-tetrabromo-3,3',5,5'-tetramethylbiphenyl and toluene diisocyanates A solution containing an 80/20 mixture of 2,4- and 2,6-toluenediisocyanates (1.74 gm, 10 mmole) and 4,4'-bis(2-hydroxyethoxy) 2,2,6,6'-tetrabromo-3,3',5,5'-tetramethylbiphenyl (6.46 gm, 10 mmole) in 25 ml of N-methylpyrolidone was prepared. DABCO, (80 mg.) was added, and the solution stirred at room temperature for 90 minutes. The resulting polymer was precipitated in methanol, filtered, redissolved in 100 ml. of chloroform and reprecipitated in methanol. Filtering and drying the material afforded 4.3 gm, 53% yield, of the polyurethane of the formula set out hereafter

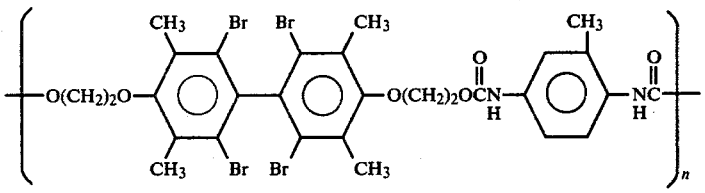

having an intrinsic viscosity (NMP + 0.1 N LiBr) of 0.13 dl/g and exhibits a glass transition of 156° C.

EXAMPLE XV

Preparation of a phosphorous containing halogenated biphenols and biphenol derivatives of TTB 19.38 gm. of 4,4'-bis(2-hydroxyethoxy)-2,2',6,6'-tetrabromo-3,3',5,5'-tetramethylbiphenyl and 4.67 ml. of triethylphosphite (0.9 molar equivalents) were heated under nitrogen at 160° for 45 minutes distilling ethanol. Vacuum (0.3 mm) was then applied for 90 minutes. Cooling afforded a glassy material which was easily broken into a free-flowing powder. The highly branched material exhibited a glass transition at 78° C. The resulting material was identified by nmr and carbon, hydrogen, oxygen, bromine and phosphorous analysis which established that a polymer having the following recurring units in the following proportions resulted from the foregoing reaction.

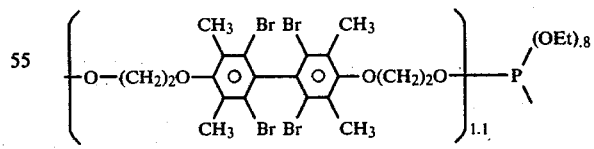

In a similar manner, in accordance with the procedure set out hereinbefore, triphenylphosphite and triphenylphosphate were reacted with 4,4'-bis(2-hydroxyethoxy)-2,2',6,6'-tetrabromo-3,3',5,5'-tetramethylbiphenyl and nmr and elemental analysis of the resulting polymers established that the following polymeric recurring units formed the skeletal backbone of the polymers from the phosphite and phosphate reactant monomer species, respectively.

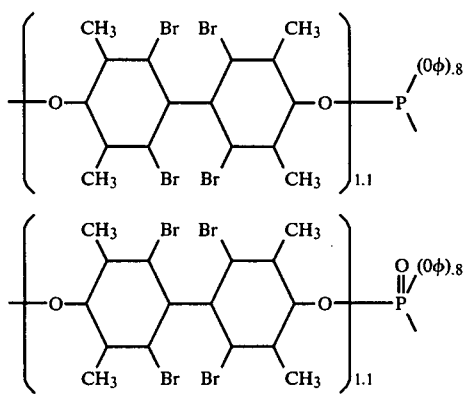

In addition to the above TTB phosphorous containing polymeric materials, other polymeric organic compounds containing TTB and TTB derivatives which contain polyphosphites and polyphosphates within the skeletal backbone of polymeric materials can also be prepared. Further, organic TTB phosphorous polymeric materials can be prepared by the reaction of suitable phosphorous compounds such as dichlorophenoxyphosphine with bis(hydroxyethoxy)tetrabromotetramethylbiphenyl under suitable reaction conditions.

The above examples illustrate wide variety of polymer systems into which TTB and its derivatives can be incorporated. The resulting polymer systems exhibit the excellent thermal and chemical stability characteristics associated with the parent TTB biphenol. The characteristic thermal and chemical stability associated with the molecular structure of the TTB is especially appreciated in high performance thermal and fire-retardant resin applications, and is more particularly appreciated in those applications requiring a flame-retardant halogen containing material to be chemically joined with the polymeric skeletal structure during preparation of a normally flammable resin structure.

The monomeric and polymeric halogenated organic compounds of our invention can be employed as flame retardant additives for normally flammable resin compositions in accordance with the teachings of our co-pending application Ser. No. 450,364; filed Mar. 12, 1974, and now U.S. Pat. No. 3,989,531 referred to hereinbefore or can be employed in the preparation of polyesters, polycarbonates, epoxy resins, polyethers, cyanurate polymers, halogenated phosphorous organic polymers, and the like.

Obviously, other modifications and variations of the present invention are possible in light of the above teachings.

What we claim as new and desire to secure by Letters Patent of the United States is:

1. A brominated biphenol selected from monomeric halogenated organo compounds of the formula

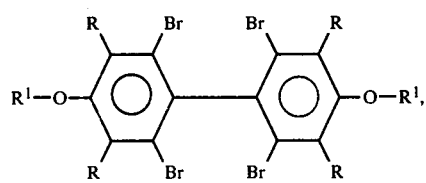

wherein independently each R is selected from primary alkyl groups, each $R^1$ is selected from hydrogen or groups identified hereafter in (a) and (b), subject to the proviso that at least one $R^1$ is selected from the group consisting of
(a) $R^2$—

$$R^4\text{-}(O\text{-}(R^3)_x)_y\text{-}\quad\text{(b)}$$

wherein $R^2$ is selected from the group consisting of alkyl, alkenyl, cycloalkyl, cycloalkenyl, aryl and mixtures thereof, $R^3$ is selected from the group consisting of alkylene, cycloalkylene, arylene and mixtures thereof, $R^4$ is selected from the group consisting of hydrogen, alkyl, alkenyl, cycloalkyl, cycloalkenyl, aryl and mixtures thereof, x is a positive integer of at least 1, and y is a positive integer of at least 1.

2. A brominated biphenol in accordance with claim 1 of the formula

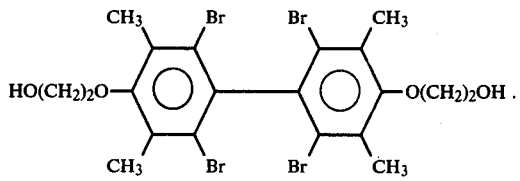

3. A brominated biphenol in accordance with claim 1 of the formula

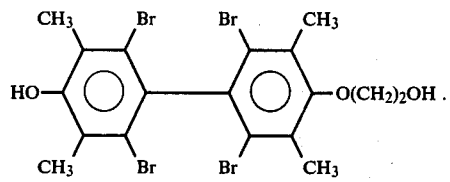

4. A brominated biphenol in accordance with claim 1 of the formula

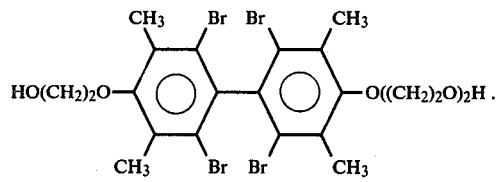

5. A brominated biphenyl of the formula

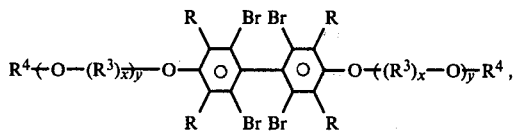

wherein independently each R is primary alkyl, each $R^3$ is selected from alkylene, cycloalkylene or arylene and mixtures thereof, each $R_4$ is selected from hydrogen, alkyl, alkenyl, cycloalkyl, cycloalkenyl, or aryl and mixtures thereof, each x is a positive integer of at least 1, and independently at least one y is a positive integer of at least 1.

6. The claim 5 compound wherein independently each R is methyl, ethyl, propyl, butyl, pentyl, hexyl, heptyl or octyl, each $R^3$ or $R^4$ contains from about 1 to about 10 carbon atoms.

7. The claim 5 compound wherein independently each R is methyl, ethyl, propyl, butyl, pentyl, hexyl, heptyl or octyl, each $R^3$ and $R^4$ contains from about 1 to about 5 carbon atoms.

* * * * *